United States Patent [19]

Tanikawa

[11] 4,403,605
[45] Sep. 13, 1983

[54] ENDOSCOPE PHOTOGRAPHING SYSTEM

[75] Inventor: Kowji Tanikawa, Hachioji, Japan

[73] Assignee: Olympus Optical Co., Ltd., Tokyo, Japan

[21] Appl. No.: 255,692

[22] Filed: Apr. 20, 1981

[30] Foreign Application Priority Data

Apr. 25, 1980 [JP] Japan ............................ 55-55008

[51] Int. Cl.³ .............................................. A61B 1/06
[52] U.S. Cl. .......................................... 128/6; 354/62
[58] Field of Search ......................... 128/6, 4; 354/62

[56] References Cited

U.S. PATENT DOCUMENTS 4,168,702 9/1979 Ohshiro .
4,281,910 8/1981 Takayama ............................ 354/62
4,284,338 8/1981 Ikuno .................................... 354/62
4,291,961 9/1981 Takayama ............................ 354/62
4,298,260 11/1981 Takayama ............................ 354/62
4,310,228 1/1982 Terada .................................. 354/62

Primary Examiner—Kyle L. Howell
Assistant Examiner—Max F. Hindenburg
Attorney, Agent, or Firm—Frishauf, Holtz, Goodman and Woodward

[57] ABSTRACT

An endoscope photographing system has a plurality of release switches respectively disposed at an endoscope, an endoscope camera, and a light source unit; and a release signal generating circuit for generating a signal in response to the operation of these release switches. When a photographing operation is being performed in response to a release signal generated in response to the operation of one of these release switches, the other release signals are disabled.

13 Claims, 5 Drawing Figures

ENDOSCOPE PHOTOGRAPHING SYSTEM

BACKGROUND OF THE INVENTION

The present invention relates to an endoscope system and, more particularly, to an endoscope photographing system having a photographing function.

Although a release button is housed within the endoscope camera in a conventional endoscope photographing system, it is more convenient if this release button is close to the endoscope control section from the perspective of ease of operation. In order to respond to this need, an endoscope photographing system has been proposed in which a release cable receiving member is incorporated in the endoscope camera for connection with an outer release cable for allowing photographing from the endoscope control section. However, such a system requires a hole for the release cable receiving member and a socket so that a waterproof structure is difficult to obtain and electrical insulation is difficult. Furthermore, if the release cable is too long, it is cumbersome. Since the release cable cannot be extended in length, the position of the release button is limited.

In U.S. Pat. No. 4,168,702, a control device of an endoscope camera is disclosed wherein release buttons are respectively disposed on the endoscope camera and the endoscope control section, and these release buttons are connected in parallel. With this device, when both of these release buttons are operated simultaneously, two photographs of the same subject may be taken.

It is, therefore, an object of the present invention to provide an endoscope system according to which the release operation may be performed at an arbitrary position and the endoscope photographing may be performed in response to a single release operation.

SUMMARY OF THE INVENTION

In an endoscope system according to the present invention, release means are arranged at a photographing device, an endoscope, and a light source unit, respectively, and means for supervising the operating conditions of these release means and photographing conditions is provided. When the system is under the photographing condition in response to the operation of one release means, a release signal or signals generated upon operation of the other release means are disabled.

This invention can be more fully understood from the following detailed description when taken in conjunction with the accompanying drawings:

BRIEF DESCRIPTION OF THE DRAWINGS

As shown in FIG. 1, an endoscope camera 13 is mounted to an eyepiece 12 of an endoscope 11, and a connector 16 at the front end of a universal cord 15 extending from a control section 14 is coupled to a light source unit 17. Release switches 18, 19 and 20 are disposed respectively on control section 14 of the endoscope 11, the endoscope camera 13, and the light source unit 17. A foot release switch 21 is also connected to the light source unit 17.

Referring to FIG. 2, the endoscope 11 is shown to include a light guide fiber optic 22 and an image guide fiber optic 23. The light guide fiber optic 22 extends from a distal end 24 of the endoscope 11 to the light source unit 17. The image guide fiber optic 23 extends from an endoscope objective lens 25 to an endoscope eyepiece lens 26. A beam splitter 27, a photographing lens 28, a shutter 29, and a film 30 are sequentially arranged in opposition to the endoscope eyepiece lens 26 in the endoscope camera 13. A photosensitive element 31 is arranged at the side surface of the beam splitter 27, and the output end of the photosensitive element 31 is connected to an I/O device 32. The release switch 19 is connected to this I/O device 32. The endoscope camera 13 also includes a reference clock signal oscillator 33, a CPU 34, a ROM 35, a RAM 36, and a transmission I/O device 37. The transmission I/O device 37 is connected to a transmission I/O device 39 of the endoscope 11 and a transmission I/O device 45 of the light source unit 17 through a transmission line 38 of the endoscope 11. The endoscope 11 also includes, as in the case of the camera 13, a reference clock signal oscillator 40, a CPU 41, a ROM 42, a RAM 43, and an I/O device 44. The light source unit 17 similarly includes a reference clock signal oscillator 46, a CPU 47, a ROM 48, a RAM 49, and an I/O device 50. To the input terminal of the I/O device 50 are connected the release switch 20 and the foot switch 21, and to the output terminal are connected a light control device 51 and a mirror driver 52. The light control device 51 is provided to control the quantity of light emitted from an observing light source 53 (e.g., a halogen lamp) and a photographing light source 54 (e.g., a strobe tube). The mirror driver 52 is provided to drive an optical path changeover mirror 55.

Referring to FIG. 2, the ROMs 35, 42 and 48 store independent main programs. Writing and reading out of information related to a series of photographing operations into and from the RAMs 36, 43 and 49 are performed in synchronism to the clock signals from the reference clock signal oscillators 33, 40 and 46.

Figure 3:
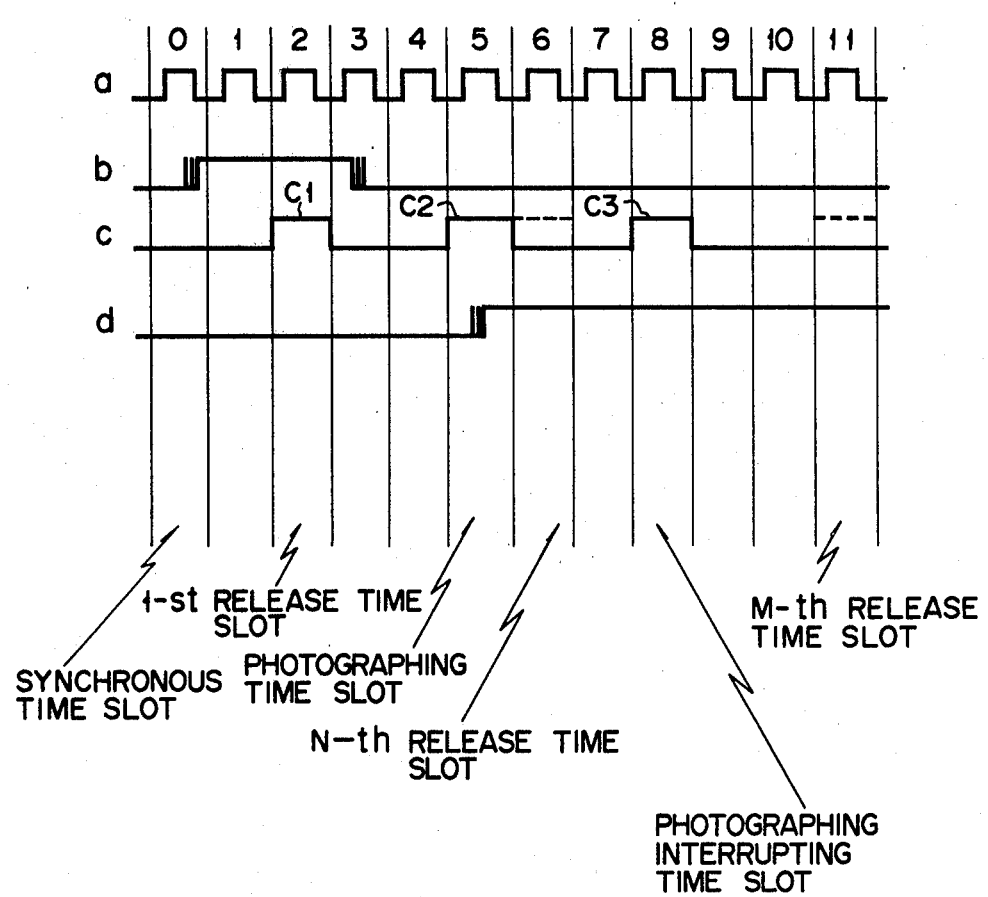
FIG. 3 shows the time slots explaining the operation of the endoscope photographing system shown in FIG. 2.
Figure 4:
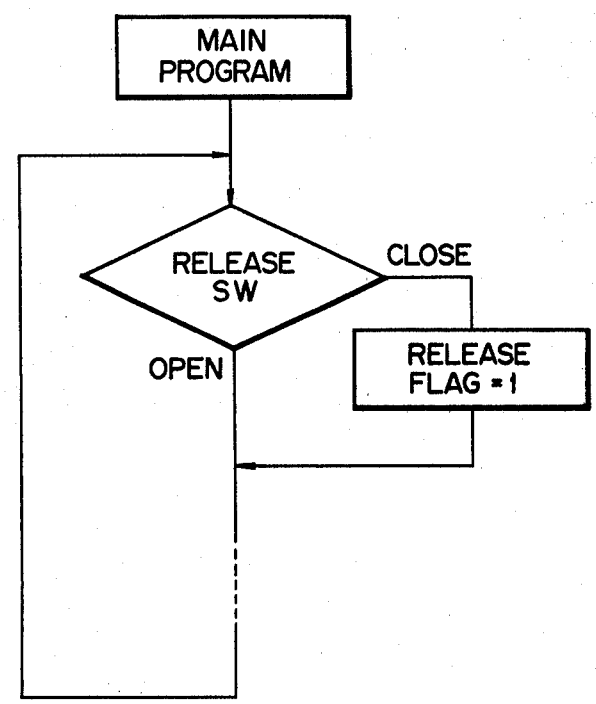
FIGS. 4 and 5 are flow charts explaining the operation of the endoscope photographing system of FIG. 2.
Figure 5:
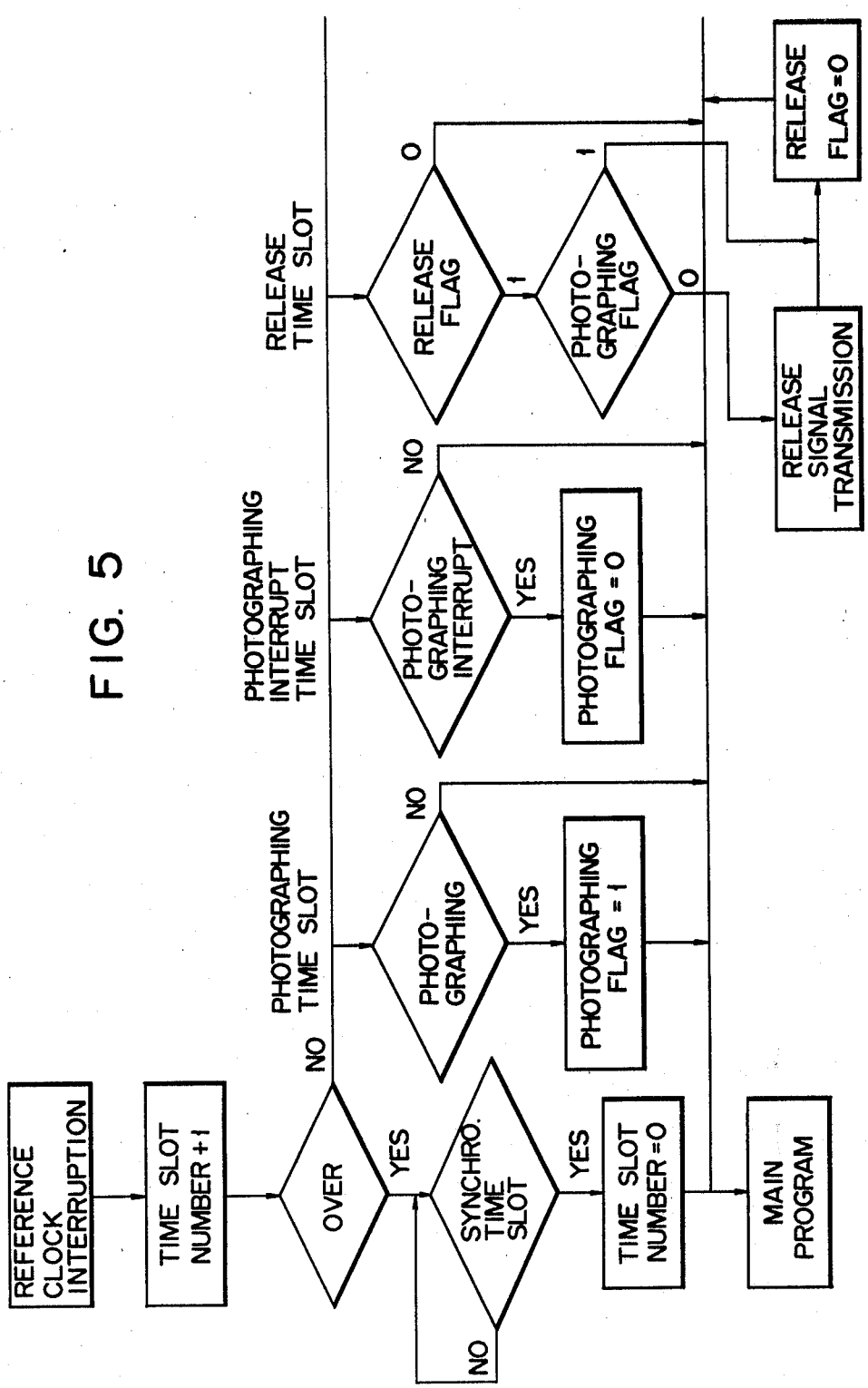

The mode of operation of the endoscope photographing system described above will be described referring to the timing chart shown in FIG. 3 and the flow charts shown in FIGS. 4 and 5. The CPUs 34, 41 and 47 of the endoscope 11, the endoscope camera 13, and the light source unit 17 supervise the signals in the transmission line through the I/O devices 37, 39 and 45 while controlling the endoscope 11, the camera 13, and the light source unit 17 according to the main programs stored in the individual ROMs 35, 42 and 48. For example, according to the main program for the endoscope camera 13, as shown in the flow chart in FIG. 4, the starting operation of the release switch 19, that is, the leading edge of the closing operation of the release switch 19, is supervised. When the release switch 19 is in the open condition, the operating systems of the endoscope camera, that is, the motor drive system, the electrical shutter system and the light measuring system, are supervised and checked for trouble. In the light source unit 17, the starting operations of the release switches 20 and 21 are similarly supervised according to the main program of the ROM 48. When the release switches 20 and 21 are in the open condition, the observing light source system, the photographing light source system, and the optical path changeover mirror system are supervised.

The CPU 47 controls and stabilizes these operating systems. The supervision and control operations according to the main programs are repeatedly performed. At the RAM 36, the clock slot number is incremented by 1 in synchronism to a reference clock signal a (FIG. 3) of the reference clock signal oscillator 33 so that the clock number is renewed according to 0, 1, 2, 3, .... For the clock slots, the clock slot numbers 2, 5 and 8 are set to be the release time slot, the time slot for the signal representing that photographing is in progress, and the time slot for the signal representing that the photographing is terminated, respectively. The time slot number of the RAM 36 is supervised by the CPU 34. It is checked by the CPU 34 to determine whether or not it has exceeded the number corresponding to the final operation of a series of photographing operations, that is, the upper limit. If the time slot number has not exceeded the upper limit, the operation for each time slot is performed. For example, the main program of the CPU 34 is interrupted by the reference clock and the CPU 34 updates the time slot number. When the time slot number is 2, the CPU 34 checks the release flag inside the RAM 36. Since the release operation is not in progress in this case, the release flag is "0". Therefore, as shown in the flow chart of FIG. 5, the main program continues. The main program is interrupted again. When the time slot number becomes 5, the photographing flag in the RAM 36 is checked. Since photographing is not in operation, the operation of the camera 13 is returned to the main program. When the time slot number 8 is reached, the photographing operation is checked to determine if it has been terminated, by judging whether the photographing flag is "0" or "1". Since the photographing flag is "0" in this case, the camera 13 executes the main program. When the time slot number reaches the number corresponding to the final operation of a series of photographing operations, that is, the upper limit, the time slot number of the RAM 36 is returned to "0" in response to the arrival of the synchronizing time slot, and the main program is executed thereafter. Under this condition, a subject 56 is illuminated by the observing light source 53, for examination.

When the release switch 19 of the camera 13 is closed under this condition, the CPU 34 detects the closure of the switch 19 through the I/O device 32 in response to the closure (FIG. 3b) of the switch 19. As a result, the CPU 34 sets the release flag of the RAM 36 to "1" and executes the main program thereafter. Then, the main program is interrupted by the reference clock and when the time slot is the release time slot, that is, the time slot 2, the release flag of the RAM 36 is checked. Since the release flag has been set to "1", the photographing flag is then checked. Since the photographing flag is "0", a release signal Cl is output from the CPU 34. This release signal Cl is transmitted to the I/O devices 39 and 45 of the endoscope 11 and the light source unit 17 through the I/O device 37 and the transmission line 38. At the light source unit 17, in response to the release signal Cl, the CPU 47 supplies a mirror changeover instruction to the mirror driver 52 to change the optical path changeover mirror 55 over to the photographing light source optical path. At the same time, at the camera 13, the shutter 29 is released by an electrical shutter driver. At the time when the shutter 29 is completely opened, the strobe tube 54 flashes and the subject 56 is photographed. Under this photographing condition, a signal C2 representing that photographing is in progress is generated at the time slot 5, and the photographing flags of the RAMs 36, 43 and 49 are set to "1". The release flag of the RAM 36 is returned to "0" when the release signal is transmitted. The release flags of the RAMs 43 and 49 are kept at "0". When, under this condition, the release switch 18 of the endoscope 11 is closed, the release flag of the RAM 43 is set to "1". The release flag of the RAM 43 is checked at the release time slot of the endoscope 11, and the photographing flag of the RAM 43 is checked since this release flag is "1". Then, the release flag is returned to "0" and the release signal is not output since the photographing flag is "1". During the photographing process, the exposure is calculated based on the output signal of the photosensitive element 31. When the right exposure is obtained, a photographing interrupting signal is transmitted to the I/O device 45 of the light source unit 17 through the transmission line 38 of the endoscope 11. In response to this photographing interrupting signal, the CPU 47 supplies to the light control device 51 an instruction to interrupt the flash radiation of the strobe tube 54. The CPU 47 also supplies to the mirror driver 52 a return instruction of the mirror 55. Then the flash radiation of the strobe tube is interrupted, and the optical path changeover mirror 55 returns to the optical path of the observing light source 53. At the same time, at the camera 13, the electrical shutter 29 is closed, and the film is wound by a motor drive. When it is confirmed at the time slot 8 that the photographing process is terminated, the photographing flags of the RAMs 36, 43, and 49 are set to "0". Even when the release switch 18 of the endoscope 11 is closed as shown by the signal d of FIG. 3, the release flag is set to "1" in response to only the leading edge of the closing operation of the release switch 18. Therefore, unless the release switch 18 is once opened and then closed, the photographing operation is not performed. It is thus possible to prevent double exposures by operator error.

In accordance with the present invention, the data transmitting function is incorporated in the endoscope photographing system so that the releasing operation of the photographing process may be performed from an arbitrary position of the camera, the endoscope and the light source device. The socket need not be incorporated in the camera, thereby making the waterproof structure simpler. Furthermore, since the photographing operation is performed in response to only one release switch even when more than one release switch is erroneously operated, two or more photographs of the same subject will not be erroneously taken. Furthermore, since a release cable is not required, the operability of the endoscope is improved. The incorporation of the foot switch allows easy release operation even when both hands are occupied. The positions for arranging the release buttons are not limited so that various kinds of switches or relays may be used without limits imposed by the space or power to be consumed.

Figure 1:
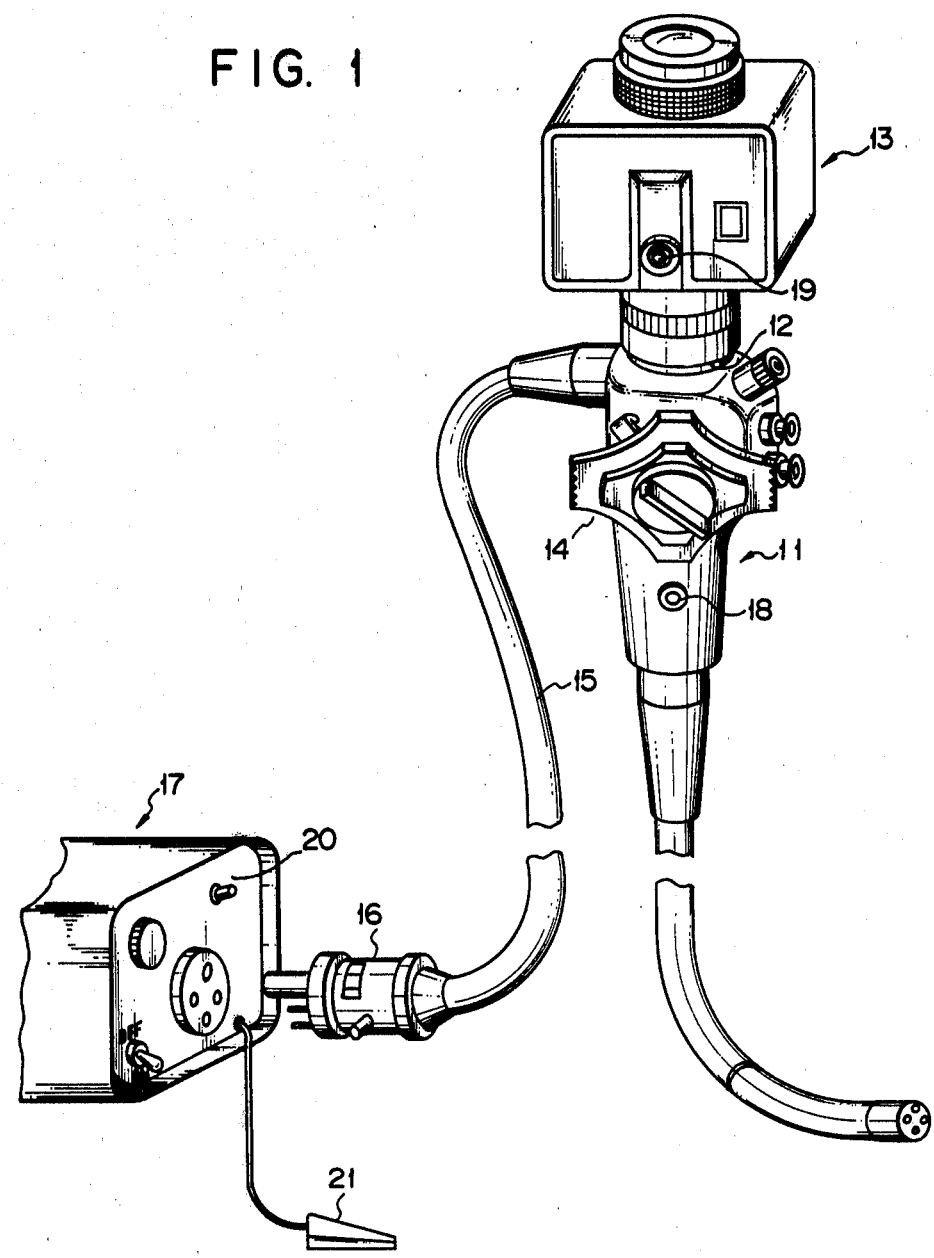
FIG. 1 is a perspective view of an endoscope photographing system according to an embodiment of the present invention.
Figure 2:
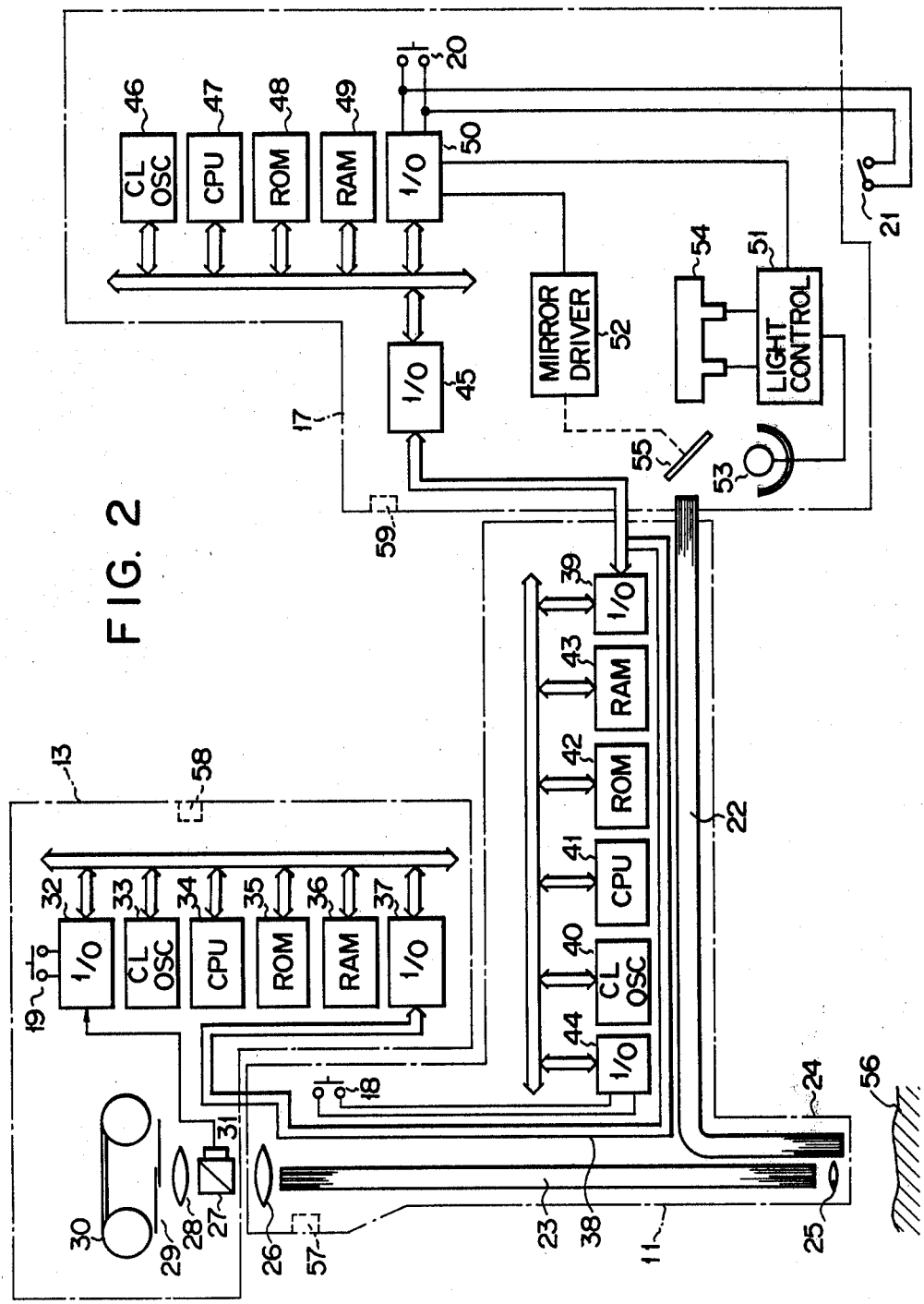
FIG. 2 is a block diagram of the endoscope photographing system shown in FIG. 1.

In the embodiment shown in FIG. 2, as shown by the dotted line indicators 57, 58 and 59 are included in the endoscope 11, the camera 13 and the light source unit 17, respectively. These indicators 57 to 59 are operated in response to the operation of the release switches 18, 19 and 20 or 21 of the endoscope 11, the camera 13, and the light source unit 17. When the endoscope photographing system is constructed in this manner, the emission of light from the indicators 57 to 59 can signal that photographing is in progress so that the double releasing operations may be prevented. The indicators may alternatively indicate that photographing is not in progress.

Although the transmission system adopted in the above embodiment was a time division data transmission system, the present invention is not limited to this, and a two-way data transmission system may alternatively be used. The release switch is not limited to a mechanical switch but may be a semiconductor switch, a photoelectric switch, an electromagnetic switch or the like. Furthermore, a voice recognition device or a particular speaker recognition device may be used. The timing signal for photographing need only be transmitted to the endoscope camera as digital data.

The present invention is not limited to endoscope cameras but may be applied to an endoscope photographing system using a video tape recorder employing a movie camera or a television camera.

What is claimed is:

1. In an endoscope photographing system which includes an endoscope, an endoscope camera optically coupled to said endoscope and a light source unit optically coupled to said endoscope, the improvement comprising:
at least two releasing means which are independently operable for initiating a photographing operation of said endoscope photographing system, each of said at least two releasing means being arranged on a respective different one of said endoscope, said endoscope camera and said light source unit;
release signal generating means coupled to each of said at least two releasing means for generating a release signal in response to the operation of any one of said releasing means;
means coupled to said release signal generating means for executing a photographing operation cycle of said endoscope photographing system in response to a release signal generated by said release signal generating means; and
means for disabling another release signal generated in response to the operation of another of said releasing means during said executing of said photographing operation cycle which was initiated responsive to operation of the first operated one of said releasing means.

2. An endoscope photographing system according to claim 1, wherein said means for executing said photographing operation cycle includes indicating means for indicating that said photographing operation cycle is being performed.

3. An endoscope photographing system according to claim 2, wherein said indicating means comprises a respective visual indicator on each of said endoscope, said endoscope camera, and said light source unit.

4. An endoscope photographing system according to claim 2, wherein said indicating means comprises at least two indicators, each of which is arranged on a respective different one of said endoscope, said endoscope camera and said light source unit.

5. An endoscope photographing system according to claim 4, wherein said indicating means comprises a respective visual indicator on each of said endoscope, said endoscope camera, and said light source unit.

6. An endoscope photographing system according to claim 1, wherein each of said endoscope, said endoscope camera, and said light source unit on which a releasing means is arranged, comprises a respective release signal generating means, a respective photographing operation executing means coupled to the associated release signal generating means, and a respective disabling means for selectively preventing operation of the associated photographing operation executing means responsive to operation of said another releasing means.

7. In an endoscope photographing system which includes an endoscope an endoscope camera optically coupled to said endoscope and a light source unit optically coupled to said endoscope, the improvement comprising:
at least three releasing means which are independently operable for initiating a photographing operation of said endoscope photographing system, each of said at least three releasing means being respectively arranged at a respective different one of said endoscope, said endoscope camera and said light source unit;
release signal generating means coupled to each of said at least three releasing means for generating a release signal in response to the operation of any one of said releasing means;
photographing means coupled to said release signal generating means for executing a photographing operation cycle of said endoscope photographing system in response to a release signal by said release signal generating means and for generating a flag signal indicating that said photographing operation is being performed; and
disabling means coupled to said photographing means and responsive to said flag signal for disabling a release signal generated in response to the operation of any of said releasing means during said photographing operation cycle.

8. An endoscope photographing system according to claim 4, wherein said photographing means further includes indicating means for indicating that said photographing operation cycle is being performed.

9. An endoscope photographing system according to claim 8, wherein said indicating means comprises a respective visual indicator on each of said endoscope, said endoscope camera, and said light source unit.

10. An endoscope photographing system according to claim 8, wherein said indicating means comprises a plurality of indicators each arranged respectively for said endoscope, said endoscope camera, and said light source unit, and each of said indicators being operative in response to a release signal from the one of said releasing means associated with the respective device which is associated with the indicating means.

11. An endoscope photographing system according to claim 10, wherein said indicating means comprises a respective visual indicator on each of said endoscope, said endoscope camera, and said light source unit.

12. An endoscope photographing system according to claim 7, wherein said photographing means comprises:
signal transmitting means for transmitting said flag signal indicating that said photographing operation is being performed by said endoscope, said endoscope camera, and said light source unit;
storing means disposed respectively at said endoscope, said endoscope camera, and said light source unit for storing said flag signal indicating that said photographing operation is being performed;
means for generating a termination signal indicating that said photographing operation is terminated when said photographing operation is terminated; and means coupled to said storing means for clearing said flag signal in said storing means in response to said termination signal representing that said photographing operation is terminated.

13. An endoscope photographing system according to claim 7, wherein each of said endoscope, said endoscope camera, and said light source unit on which a releasing means is arranged, comprises a respective release signal generating means, a respective photographing operation executing means coupled to the associated release signal generating means, and a respective disabling means for selectively preventing operation of the associated photographing operation executing means responsive to operation of said another releasing means.

* * * * *